United States Patent
Ionasec (10) Patent No.: US 10,540,480 B2
(45) Date of Patent: Jan. 21, 2020

(54) MEDICAL IMAGING SYSTEM

(71) Applicant: Siemens Healthcare GmbH, Erlangen (DE)

(72) Inventor: Razvan Ionasec, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 72 days.

(21) Appl. No.: 15/682,609

(22) Filed: Aug. 22, 2017

(65) Prior Publication Data

US 2018/0060490 A1     Mar. 1, 2018

(30) Foreign Application Priority Data

Aug. 29, 2016   (DE) .................. 10 2016 216 203

(51) Int. Cl.

| | | |
|---|---|---|
| *G06K 9/00* | (2006.01) | |
| *G06F 19/00* | (2018.01) | |
| *A61B 6/03* | (2006.01) | |
| *G16C 20/90* | (2019.01) | |
| *G16H 40/63* | (2018.01) | |

(52) U.S. Cl.
CPC ............ *G06F 19/321* (2013.01); *A61B 6/032* (2013.01); *G06F 19/3418* (2013.01); *G16C 20/90* (2019.02); *G16H 40/63* (2018.01)

(58) Field of Classification Search
None
See application file for complete search history.

(56) References Cited

U.S. PATENT DOCUMENTS

| | | | | |
|---|---|---|---|---|
| 6,006,231 A | * | 12/1999 | Popa ............... | G06F 17/30905 |
| 8,189,002 B1 | * | 5/2012 | Westerhoff .......... | G06T 15/005 |
| | | | | 345/419 |
| 8,879,813 B1 | * | 11/2014 | Solanki ............. | G06T 7/0014 |
| | | | | 382/128 |
| 2002/0158912 A1 | * | 10/2002 | O'Rourke ........... | G06F 3/0481 |
| | | | | 715/810 |
| 2004/0015079 A1 | * | 1/2004 | Berger .............. | A61B 8/546 |
| | | | | 600/437 |
| 2004/0041563 A1 | * | 3/2004 | Lewin .............. | G01R 33/022 |
| | | | | 324/307 |
| 2004/0202360 A1 | * | 10/2004 | Besson ............. | G06T 5/008 |
| | | | | 382/131 |

(Continued)

OTHER PUBLICATIONS

Wikipedia: "Common Object Request Broker Architecture"; aus Wikipedia, der freien Enzyklopädie; Version zuletzt bearbeitet am Mar. 21, 2016.

(Continued)

*Primary Examiner* — Shervin K Nakhjavan
(74) *Attorney, Agent, or Firm* — Harness, Dickey & Pierce, P.L.C.

(57) ABSTRACT

A medical imaging system includes a medical imaging device for generating image data. The medical imaging device includes a first programming interface for transferring the image data and a second programming interface for transferring the supplementary data. The medical imaging system further includes a processing device for retrieving the image data and the associated supplementary data from the medical imaging device and for carrying out a further processing based upon the image data and the supplementary data.

18 Claims, 1 Drawing Sheet

(56) References Cited

U.S. PATENT DOCUMENTS

| | | | |
|---|---|---|---|
| 2005/0203771 A1* | 9/2005 | Achan | G06Q 10/103 705/2 |
| 2005/0240445 A1* | 10/2005 | Sutherland | G06F 19/321 705/3 |
| 2007/0043535 A1* | 2/2007 | Belden | G06F 11/349 702/183 |
| 2008/0052112 A1* | 2/2008 | Zahlmann | G06F 19/321 705/2 |
| 2008/0270177 A1* | 10/2008 | Chamberlain | G06F 19/321 705/2 |
| 2009/0025016 A1* | 1/2009 | Crucs | G06F 17/212 719/329 |
| 2009/0318800 A1* | 12/2009 | Gundel | A61B 5/02007 600/425 |
| 2011/0087651 A1* | 4/2011 | Westin | G06F 19/321 707/722 |
| 2013/0093829 A1* | 4/2013 | Rosenblatt | G09B 5/00 348/14.01 |
| 2013/0204976 A1* | 8/2013 | Okuyama | G06F 19/321 709/219 |
| 2013/0281825 A1 | 10/2013 | Thiruvenkadam et al. | |
| 2014/0072192 A1* | 3/2014 | Reiner | G06T 7/0012 382/128 |
| 2014/0109239 A1* | 4/2014 | Flint | H04L 63/10 726/27 |
| 2014/0207514 A1* | 7/2014 | Domke | G06Q 10/20 705/7.26 |
| 2015/0052058 A1* | 2/2015 | McCown | G06Q 50/22 705/51 |
| 2015/0201906 A1* | 7/2015 | Yoshida | A61B 8/5207 600/424 |
| 2015/0220686 A1* | 8/2015 | Rodriguez | G16H 10/60 726/4 |
| 2015/0278207 A1* | 10/2015 | Seo | G06F 16/51 348/231.2 |
| 2015/0379199 A1* | 12/2015 | Tambasco, Jr. | H04N 5/44 705/3 |
| 2016/0228034 A1* | 8/2016 | Gluncic | G06K 9/00 |
| 2017/0035514 A1* | 2/2017 | Fox | G06F 19/321 |
| 2017/0109757 A1* | 4/2017 | Tuchman | H04L 63/104 |
| 2017/0168812 A1* | 6/2017 | Golay | G06F 8/654 |
| 2019/0043195 A1* | 2/2019 | Buelow | G16H 30/20 |

OTHER PUBLICATIONS

Wikipedia: "Programmierschnittstelle"; aus WIklpecila, der frelen Enzyklopädie; Version zuletzt am Jan. 1, 2016 geändert.
German Office Action dated Jan. 2, 2017.

* cited by examiner

MEDICAL IMAGING SYSTEM

PRIORITY STATEMENT

The present application hereby claims priority under 35 U.S.C. § 119 to German patent application number DE 102016216203.9 filed Aug. 29, 2016, the entire contents of which are hereby incorporated herein by reference.

FIELD

At least one embodiment of the present invention generally relates to a medical imaging system with a medical imaging device for generating image data.

BACKGROUND

Current medical imaging devices and a pre- and post-processing equipment generate, aside from the actual image data, a growing quantity of useful data, which can supplement the image data and be used for a further processing. This supplementary data is currently only used in the closed low-level system components within the medical imaging device and is not employed by specialized high-level algorithms and applications in external processing devices.

Medical imaging devices generate a large quantity of measurement data. In the case of CT scanners, measurement data of this type comprises sinograms which are obtained at different spatial, temporal or energy locations. This supplementary data (rich data or augmented data) is processed internally in the medical imaging device, while only standardized image reconstructions are provided in the form of DICOM image series for external processing devices. The supplementary data is not made accessible to the external processing devices which are connected to the medical imaging device.

Different algorithms of external processing devices would however be able to further process not only image data but also the supplementary data, for an image processing for instance. In the case of a CT scanner, the supplementary data may comprise different data relating to dual-energy classes, a spectral imaging, an iterative reconstructed imaging, a segmentation and labeled data. The labeled data identifies specific organs or anatomical areas in the associated image data for instance.

Typically the supplementary data is processed internally by the medical imaging device and is not transferred to the external processing devices. The performance capability of data-dependent applications and algorithms of artificial intelligence nevertheless depends heavily on the quality and quantity of data, which is used as input parameters.

SUMMARY

At least one embodiment of the present invention improves the external data processing in a medical imaging system.

Advantageous embodiments form the subject matter of the claims, the description and the figures.

According to a first embodiment, a medical imaging system includes a medical imaging device for generating image data, which comprises a first programming interface for transferring the image data and a second programming interface for transferring the associated supplementary data, and a processing device for retrieving the image data and the associated supplementary data from the medical imaging device and for carrying out a further processing on the basis of the image data and the supplementary data. The medical imaging system, in at least one embodiment, achieves the technical advantage that the supplementary data of the medical imaging device is available for a recalculation or further processing on the processing device.

According to a second embodiment, a medical imaging device for generating image data on the basis of recorded supplementary data comprises a first programming interface for transferring the image data and a second programming interface for transferring the supplementary data. The same technical advantages are achieved by the medical imaging device as by the medical imaging system according to the first embodiment.

According to a third embodiment, a method for carrying out a further processing of medical data includes retrieving image data by way of a first programming interface and associated supplementary data by way of a second programming interface of a medical imaging device; and carrying out the further processing on the basis of the image data and the supplementary data. The same technical advantages are achieved by the method as by the medical imaging system according to the first embodiment.

BRIEF DESCRIPTION OF THE DRAWINGS

Example embodiments of the invention are shown in the drawings and are described in more detail below, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment, a medical imaging system includes a medical imaging device for generating image data, which comprises a first programming interface for transferring the image data and a second programming interface for transferring the associated supplementary data, and a processing device for retrieving the image data and the associated supplementary data from the medical imaging device and for carrying out a further processing on the basis of the image data and the supplementary data. The medical imaging system, in at least one embodiment, achieves the technical advantage that the supplementary data of the medical imaging device is available for a recalculation or further processing on the processing device.

In an advantageous embodiment of the medical imaging system, the medical imaging device comprises a database for retrieving the image data and/or the supplementary data. As a result, the technical advantage is achieved for instance in that the image data and/or the supplementary data can be retrieved with minimal access times.

In a further advantageous embodiment of the medical imaging system, the database for retrieving the image data is implemented on a server within the medical imaging device. As a result, the technical advantage is achieved for instance that the database can be provided on the server irrespective of the medical imaging device.

In a further advantageous embodiment of the medical imaging system, the processing device is embodied to retrieve the supplementary data as a function of a further processing task to be carried out. As a result, the technical advantage is achieved for instance that the data volume to be transmitted is reduced.

In a further advantageous embodiment of the medical imaging system, the processing device is embodied to retrieve the supplementary data as a function of an executed application. As a result, the technical advantage is likewise achieved for instance that the data volume to be transmitted is reduced.

In a further advantageous embodiment of the medical imaging system, the processing device is embodied to define a format of the supplementary data. As a result, the technical advantage is likewise achieved for instance that the data can be efficiently transmitted.

In a further advantageous embodiment of the medical imaging system, the processing device is embodied to send an application-specific programming interface definition to the medical imaging device. As a result, the technical advantage is likewise achieved for instance that the programming interfaces can be individually adapted.

In a further advantageous embodiment of the medical imaging system, the supplementary data comprises raw data of the medical imaging examination. As a result, the technical advantage is likewise achieved for instance that the image data can be completely recalculated.

In a further advantageous embodiment of the medical imaging system, the supplementary data comprises data which has been recorded with a microphone or an optical camera. As a result, the technical advantage is likewise achieved for instance that optical or acoustic data can be taken into account.

In a further advantageous embodiment of the medical imaging system, the supplementary data comprises scan parameters of the medical examination or reconstruction parameters of the image data. As a result, the technical advantage is likewise achieved for instance that image data can be further processed by taking the scan parameters or the reconstruction parameters into account.

In a further advantageous embodiment of the medical imaging system, the second programming interface provides functions for retrieving predetermined supplementary data. As a result, the technical advantage is likewise achieved for instance that specific supplementary data can be targetedly retrieved.

In a further advantageous embodiment of the medical imaging system, the processing device is formed by a terminal computer, a software client or a cloud-based application. As a result, the technical advantage is likewise achieved for instance that suitable devices are used to further process the data.

In a further advantageous embodiment of the medical imaging system, the medical imaging device is a magnetic resonance scanner or a computed tomography scanner. As a result, the technical advantage is likewise achieved for instance that suitable devices are used to record the supplementary data.

According to a second embodiment, a medical imaging device for generating image data on the basis of recorded supplementary data comprises a first programming interface for transferring the image data and a second programming interface for transferring the supplementary data. The same technical advantages are achieved by the medical imaging device as by the medical imaging system according to the first embodiment.

According to a third embodiment, a method for carrying out a further processing of medical data includes retrieving image data by way of a first programming interface and associated supplementary data by way of a second programming interface of a medical imaging device; and carrying out the further processing on the basis of the image data and the supplementary data. The same technical advantages are achieved by the method as by the medical imaging system according to the first embodiment.

Figure 1:
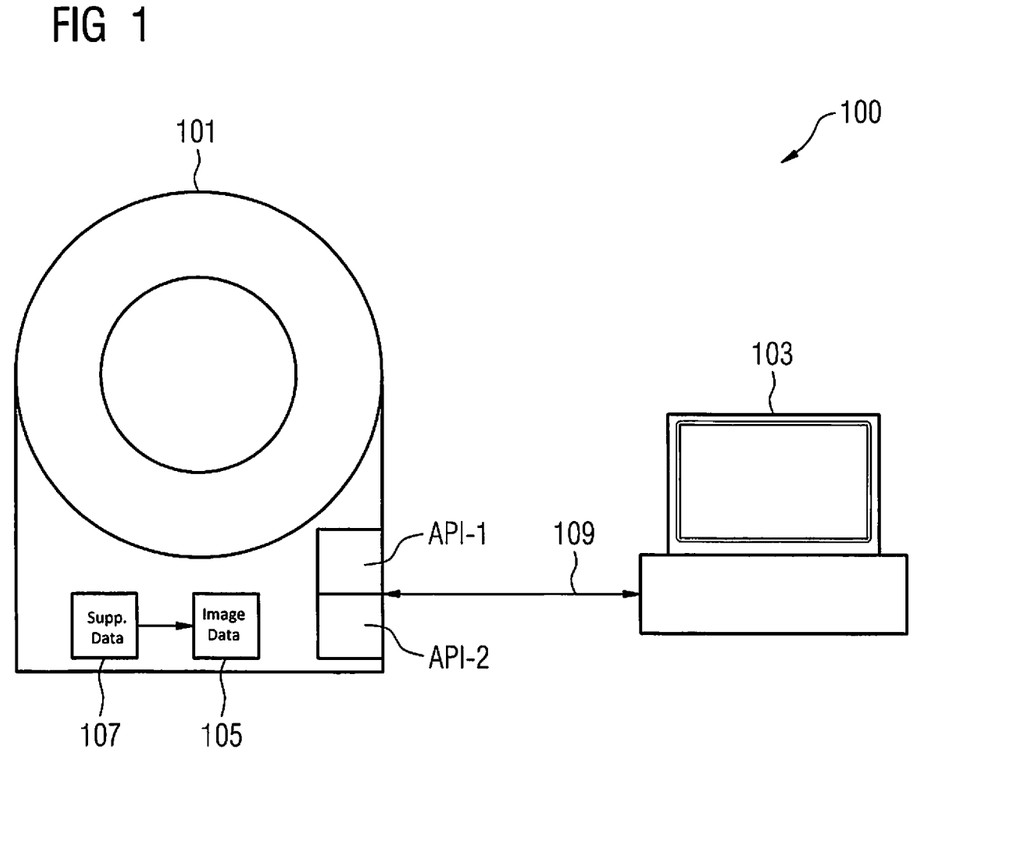
FIG. 1 shows a schematic representation of a medical imaging system.

FIG. 1 shows a schematic representation of a medical imaging system 100. The imaging system 100 allows supplementary data to be retrieved from the imaging device 101 by an external processing device 103, on which external applications and algorithms can be executed.

The imaging device 101 is a magnetic resonance scanner or a computed tomography scanner, for instance in the form of a smart scanner, which can generate other data as raw recording data or DICOM data. The scanner calculates the supplementary data and provides this by way of a programming interface API-2. The supplementary data supplements the associated image data with further information. In such cases the image data is located in the same coordinate system as the supplementary data and is attuned herewith.

The imaging device 101 records a plurality of supplementary data 107 during the medical examination using a data processing unit. The supplementary data 107 is encapsulated in a predetermined data format.

The image data 105 is calculated from the supplementary data 107, such as DICOM files for instance. With this calculation of the image data 105, a loss of information often takes place compared with the supplementary data 107. For this purpose, the imaging device 100 comprises a processor and a storage unit, by means of which the supplementary data 107 can be processed in the image data 105. Both the image data 105 and also the supplementary data 107 are stored in a non-volatile storage unit in the imaging device 101, such as in a database for instance.

The imaging device 101 comprises two programming interfaces API-1 and API-2 (API—Application Programming Interface). The programming interfaces API-1 and API-2 are formed by program parts, which are made available by the software system of the imaging device 101 to other programs for connection purposes.

The programming interface API-1 provides access to the generated image data 105. The programming interface API-2 provides access to the supplementary data 107 based on different input parameters or requests.

Moreover, the medical imaging system 100 comprises an infrastructure 109, in order to transfer the image data 105 and also the supplementary data 107 at high speed to a remote processing device 103, such as a terminal computer for instance. The infrastructure 109 comprises a data line for instance, by way of which any data can be transferred between the processing device 103 and the imaging device 101. On account of the infrastructure 109 and the programming interfaces API-1 and API-2, the image data 105 and the supplementary data 107 can be made available at a desired location.

The processing device 103 likewise comprises a storage unit and a processor for further processing the image data 105 and the supplementary data 107, which is retrieved by way of the programming interfaces API-1 and API-2 of the imaging device 101.

The different types of supplementary data 107 can comprise the following information:

The supplementary data 107 can comprise multi-parameter information including information relating to a number of energy levels, a functional imaging and time-resolved images (energy thresholds and a subpixel/macropixel mode in the case of a photon counter).

The supplementary data 107 can be supplemented with information with regard to image quality and image content.

The supplementary data 107 can comprise a geometric object, which represents a location or a shape of organs in the image data 105.

The supplementary data 107 can comprise an identifier of image data 105 with regard to an anatomic ontology and/or material or tissue ontologies.

The supplementary data 107 can comprise individually adjusted properties in respect of spatial, temporal, noise and other basic parameters.

The supplementary data 107 can comprise data which has been recorded with a microphone or an optical camera.

The supplementary data 107 can comprise scan parameters (gradient, pitch, rotation time, couch advance, current, acceleration voltage) and reconstruction parameters (selection of the convolution matrix (kernel), matrix size, iterative reconstruction).

The supplementary data 107 can be adjusted individually to requirements which are predefined by a specific application or a specific algorithm in the processing device 103, such as for instance by dedicated reconstructions or another processing.

A technical implementation can take place as follows:

The supplementary data 107—such as for instance noise properties, identifying characteristics and remarks, raw data, retrieved parameters (e.g. iodine uptake), scan parameters or reconstruction parameters, are stored in a database on a server within the imaging device 101.

The server is configured to transfer the supplementary data 107 on request (data-as-a-service) to the processing device 103. The processing device 103 can be formed by a software client or a cloud-based application.

The processing device 103 at a remote location is used to calculate the medical image data 105 for the purpose of a recording, a segmentation, a clustering, a merging/registration or a simulation of patient-specific data.

Complementary programming interfaces to the programming interfaces API-1 and API-2 are implemented in a code in the remote processing device 103 for the purpose of retrieving the supplementary data 107 and the image data 105 for a specific task.

The processing device 103 is connected to the server or the database of the imaging device 101.

The processing device 103 selects specific supplementary data 107 from the database for a defined task and selects corresponding function calls of the programming interface API-2 for retrieving the supplementary data 107.

A file with an application-specific programming interface definition is received at the server.

The supplementary data 107 is transferred to the remote processing device 103.

A processing of medical images based on the image data 105 (DICOM data) and also the additionally retrieved supplementary data 107 is carried out on the remote processing device 103.

A provision of the data can optionally be submitted either per call or on the basis of the data quantity.

The server can optionally offer proposals, which are most suited to supplementary data 107 for the selected application.

One example of using supplementary data 107 from the CAD area resides in a knowledge about reconstruction parameters (sharp/smooth convolution matrix) which potentially contributes to making a distinction between a noise and small anatomical structures, such as blood vessels for instance.

One further example from the field of patient-specific simulation includes a knowledge about a patient anatomy, which may have a disadvantageous effect on the simulation results, such as a lumen diameter for instance. Image data 105 can be reconstructed with more suitable convolution matrices on the basis of the supplementary data 107 or known artifacts or an image quality can be taken into account.

One further example from the area of training of databases for machine-learning methods resides in all entries in the database being able to be reconstructed with the same parameters for the purpose of consistency.

Figure 2:
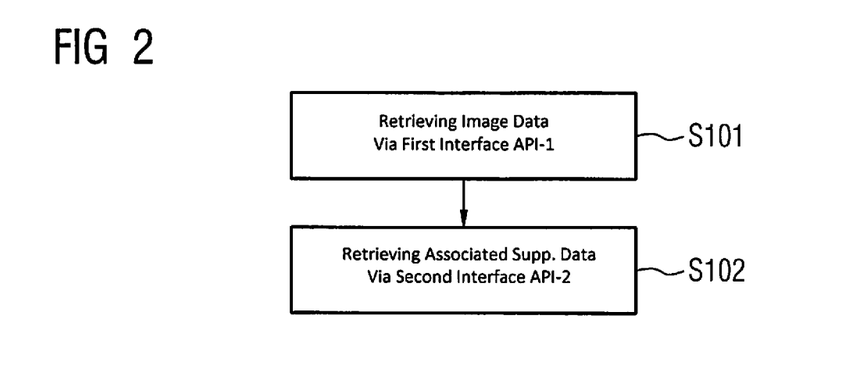
FIG. 2 shows a block diagram of a method.

FIG. 2 shows a block diagram of the method for carrying out a further processing of medical data on an external processing device. The method comprises the steps S101 of retrieving image data 105 by way of the first programming interface API-1 and an additional retrieval of associated supplementary data 107 by way of the second programming interface API-2 of the medical imaging device 101 and the step S102 of carrying out the further processing on the basis of the retrieved image data 105 and the additionally retrieved supplementary data 107.

The advantages of the medical imaging system 100 and the method lie in the additional provision of obtained supplementary data 107 for external processing devices 103, so that external applications and algorithms on these processing devices 103 can process the additional information. A standard can be established, in order to transfer the supplementary data, which has been obtained by the medical imaging device, for further processing. Furthermore, new access models can be implemented, which are linked with the data and the access to the data.

All features shown and explained in conjunction with the individual embodiments of the invention can be provided in a different combination in the inventive subject matter in order at the same time to realize its advantageous effects.

All method steps can be implemented by apparatuses which are suited to executing the respective method step. All functions which are carried out by the objective features can be a method step of a method.

The scope of protection of the present invention is provided by the claims and is not restricted by the features explained in the description or shown in the figures.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical imaging system, comprising:
a medical imaging device to generate image data and store associated supplementary data, the medical imaging device including a first programming interface to transfer the image data and a second programming interface to transfer the associated supplementary data, the medical imaging device being a magnetic resonance scanner or a computed tomography scanner, the associated supplementary data being a plurality of different information types associated with image quality and content of the image data; and
a processor configured to
select at least one information type of the associated supplementary data for retrieval and select corresponding function calls for the second programming interface,
retrieve the image data and the selected associated supplementary data from the medical imaging device, and
carry out a further processing based on the image data and the selected associated supplementary data.

2. The medical imaging system of claim 1, wherein the medical imaging device further comprises a database to retrieve at least one of the image data and the associated supplementary data.

3. The medical imaging system of claim 2, wherein the database to retrieve the image data is implemented on a server within the medical imaging device.

4. The medical imaging system of claim 2, wherein the processor is configured to retrieve the selected associated supplementary data as a function of a further processing task to be carried out.

5. The medical imaging system of claim 2, wherein the processor is configured to retrieve the selected associated supplementary data as a function of an executed application.

6. The medical imaging system of claim 1, wherein the processor is configured to select and retrieve the selected associated supplementary data based on a determination associated with the further processing.

7. The medical imaging system of claim 1, wherein the processor is configured to retrieve the selected associated supplementary data as a function of an executed application.

8. The medical imaging system of claim 1, wherein the processor is configured to define a format of the associated supplementary data.

9. The medical imaging system of claim 1, wherein the processor is configured to send an application-specific programming interface definition to the medical imaging device.

10. The medical imaging system of claim 1, wherein the associated supplementary data includes raw data of a medical imaging examination.

11. The medical imaging system of claim 1, wherein the associated supplementary data includes data which has been recorded with a microphone or an optical camera.

12. The medical imaging system of claim 1, wherein the associated supplementary data includes scan parameters of a medical examination or reconstruction parameters of the image data.

13. The medical imaging system of claim 1, wherein the plurality of different information types associated with image quality and content of the image data includes
scan parameters of a medical imaging examination or reconstruction parameters of the image data,
raw data of a medical imaging examination,
multi-parameter information, the multi-parameter information including information relating to a number of energy levels, a functional imaging and time-resolved images,
a geometric object, the geometric object representing a location or a shape of organs in the image data,
an identifier of the image data with regard to an anatomic ontology, a material or tissue ontologies,
adjustable properties associated with spatial, temporal, and noise parameters,
data which has been recorded with a microphone or an optical camera,
scan parameters, the scan parameters being a gradient, a pitch, a rotation time, a couch advance, a current, a acceleration voltage, or a combination thereof, and
reconstruction parameters, the reconstruction parameters being a selection of a convolution matrix or kernel, a matrix size, a iterative reconstruction, or a combination thereof.

14. The medical imaging system of claim 1, wherein the medical imaging device is a computed tomography scanner.

15. A medical imaging device comprising:
a non-transitory memory having computer-readable instructions stored thereon; and
at least one processor configured to execute the computer-readable instructions to cause the medical imaging device to
generate image data based upon recorded supplementary data, wherein the recorded supplementary data is a plurality of different information types associated with image quality and content of the image data;
transfer the image data by a first programming interface; and
transfer selected recorded supplementary data by a second programming interface, the selected recorded supplementary data being one of a partial or full set of the recorded supplementary data.

16. A medical imaging system, comprising the medical imaging device of claim 15.

17. The medical imaging system of claim 16, wherein the medical imaging device is a magnetic resonance scanner or a computed tomography scanner.

18. A method for carrying out a further processing of medical data, comprising:
retrieving image data by way of a first programming interface implemented by at least one processor of a medical imaging device and retrieving selected associated supplementary data by way of a second programming interface implemented by the at least one processor of the medical imaging device, retrieving the selected associated supplementary data includes selecting specific information types of associated supplementary data for retrieval and selecting corresponding function calls for the second programming interface, wherein the associated supplementary data is a plurality of different information types associated with image quality and content; and
carrying out the further processing based upon the image data and the associated supplementary data.

* * * * *